(12) United States Patent
Hartman et al.

(10) Patent No.: US 7,566,495 B2
(45) Date of Patent: *Jul. 28, 2009

(54) ANTIMICROBIAL COMPOSITES, FILMS, LABELSTOCKS, AND LABELS

(75) Inventors: William G. Hartman, North Royalton, OH (US); Chan U. Ko, Arcadia, CA (US)

(73) Assignee: Avery Dennison Corporation, Pasadena, CA (US)

( * ) Notice: Subject to any disclaimer, the term of this patent is extended or adjusted under 35 U.S.C. 154(b) by 576 days.

This patent is subject to a terminal disclaimer.

(21) Appl. No.: 10/965,559

(22) Filed: Oct. 14, 2004

(65) Prior Publication Data

US 2005/0106121 A1 May 19, 2005

Related U.S. Application Data

(60) Provisional application No. 60/514,188, filed on Oct. 24, 2003.

(51) Int. Cl.
*B32B 7/12* (2006.01)

(52) U.S. Cl. ...................... 428/343; 428/351

(58) Field of Classification Search ................. 428/343, 428/351
See application file for complete search history.

(56) References Cited

U.S. PATENT DOCUMENTS

| | | | | |
|---|---|---|---|---|
| 3,208,875 A | * | 9/1965 | Holden | 427/246 |
| 3,780,140 A | | 12/1973 | Hammer | 260/884 |
| 4,400,374 A | * | 8/1983 | Cardarelli | 424/486 |
| 4,547,381 A | | 10/1985 | Mason et al. | 426/316 |
| 4,869,905 A | * | 9/1989 | Sobek et al. | 424/406 |
| 5,071,704 A | * | 12/1991 | Fischel-Ghodsian | 428/354 |
| 5,360,609 A | | 11/1994 | Wellinghoff | 514/772.3 |
| 5,631,300 A | | 5/1997 | Wellinghoff | 514/772.3 |
| 5,914,120 A | | 6/1999 | Wellinghoff et al. | 424/406 |
| 5,974,810 A | | 11/1999 | Speronello | 62/66 |
| 5,980,826 A | | 11/1999 | Barenberg et al. | 422/37 |
| 6,077,495 A | | 6/2000 | Speronello et al. | 423/477 |
| 6,132,748 A | | 10/2000 | Khanna et al. | 424/405 |
| 6,238,643 B1 | | 5/2001 | Thangaraj et al. | 423/477 |
| 6,294,108 B1 | | 9/2001 | Speronello et al. | 252/187.21 |
| 2001/0036421 A1 | | 11/2001 | Speronello et al. | 422/4 |
| 2002/0036284 A1 | | 3/2002 | Speronello et al. | 252/187.21 |
| 2003/0021819 A1 | | 1/2003 | Khanna et al. | 424/405 |

FOREIGN PATENT DOCUMENTS

| | | |
|---|---|---|
| WO | 90/13600 | 11/1990 |
| WO | 00/32052 | 6/2000 |

OTHER PUBLICATIONS

Aseptrol® tablets; Engelhard; Product Information Sheet; Rev. Apr. 2003.
Styron 615APR; Dow Plastics; Product Information Sheet; pp. 1-3.
Estane; Product Data for Estane® 5714 TPU; Noveon; 2001.
Kraton® Polymers for use in adhesive and sealant applications; pp. 14-18.

* cited by examiner

*Primary Examiner*—Victor S Chang

(57) ABSTRACT

This invention relates to antimicrobial composites, films, labelstocks and labels. The antimicrobial composites comprise (A) a polymer mixture comprising a mixture of at least one styrene polymer and at least one urethane polymer, and (B) an antimicrobial composition which comprises at least one metal chlorite and at least one hydrophilic material capable of reacting with the metal chlorite when exposed to water. The composites which are described herein are useful in preparing films, labelstocks and labels which exhibit the desirable antimicrobial properties by providing a controlled release of chlorine dioxide gas over an extended period of time.

46 Claims, No Drawings

ANTIMICROBIAL COMPOSITES, FILMS, LABELSTOCKS, AND LABELS

CROSS REFERENCE TO RELATED APPLICATION

This application claims priority from provisional application Ser. No. 60/514,188 filed Oct. 24, 2003. The provisional application is hereby incorporated in its entirety by reference.

TECHNICAL FIELD OF THE INVENTION

This invention relates to antimicrobial composites which are useful for the controlled release of chlorine dioxide gas, and more particularly, to the use of such antimicrobial composites for preparing films, labelstocks and labels which provide for a controlled release of chlorine dioxide gas.

BACKGROUND OF THE INVENTION

Chlorine dioxide is known to be a disinfectant as well as a strong oxidizing agent. The bactericidal, algecidal, fungicidal, bleaching and deodorizing properties of chlorine dioxide also are well known.

Gaseous chlorine dioxide in low concentrations such as up to about 1000 ppm has been recognized as useful for the treatment of odors and microbes. Thus, chlorine dioxide is commonly used as a disinfectant or fumigant in a number of applications and environments. Chlorine dioxide is particularly useful for the control of microbes and/or organic deodorants on and around food products during and after the packaging process. It has been reported that chlorine dioxide functions without the formation of undesirable side products such as chloramines or chlorinated organic compounds that can be produced when elemental chlorine is utilized. For example, a low concentration of chlorine dioxide gas can be maintained in contact with fresh produce for several days during shipping from the farm to the local retailer thereby reducing the rate of spoilage of the produce. In addition, chlorine dioxide gas is considered to be safe for human contact at the low concentrations that are effective for deodorization and for most antimicrobial applications.

The chlorine dioxide gas can be toxic to humans at concentrations greater than about 1000 ppm, and it can be explosive at concentrations above 0.1 atmosphere. Therefore, chlorine dioxide gas is not manufactured and shipped under pressure like other industrial gases, and conventional methods of on-site manufacture require not only expensive equipment, but also high levels of operator skill to avoid generating dangerously high concentrations.

It has been suggested that the chlorine dioxide which is useful for the treatment of odors and microbes can be generated from metal chlorites such as sodium chlorite, and compositions have been suggested which comprise mixtures of metal chlorides and other solid materials where the chlorine dioxide gas may be generated under control conditions at low concentrations. For example, it has been suggested that such mixtures of chlorites and solid materials can be maintained for an extended period of time without generation of chloride dioxide until exposed to an activating agent such as water, and when exposed to water, the compositions provide a controlled and sustained release of chlorine dioxide gas. Accordingly, such compositions can be prepared in advance and stored under dry conditions without the premature release of chlorine dioxide gas. In this manner, the requirement for skilled personnel to prepare the chlorine dioxide on site is avoided, and shelf life is enhanced.

U.S. Pat. No. 6,077,495 describes a method, composition and system for generating chlorine dioxide gas in a control release manner by combining at least one metal chlorite and a dry solid hydrophilic material which reacts with the metal chlorite in the presence of water vapor, but does not react with the metal chlorite in the substantial absence of liquid water or water vapor, to produce chlorine dioxide gas in a sustained amount of from about 0.01 to 1000 ppm.

U.S. Pat. No. 5,631,300 describes a process for preparing a composite for preventing growth of bacteria, molds, fungi and viruses by dissolving a chlorite salt in an organic hydrophilic material, and then mixing the hydrophilic material with a hydrophobic material containing an acid releasing agent. U.S. Pat. No. 5,914,120 describes composite for controlling microbiological contamination which comprises a hydrophilic material containing an alpha-amino ether, alpha-amino alcohol or alpha-amino ester and a chlorite salt, and a hydrophobic material containing an acid releasing agent. The hydrophilic material is described as being capable generating and releasing chlorine dioxide gas after hydrolysis of the acid releasing agent. U.S. Pat. No. 5,980,826 describes a method for retarding bacterial, fungal and viral contamination and growth in molds on the surface of a material and/or deodorizing the material by treating a surface with a composite which does not release chlorine dioxide in the absence of moisture, and thereafter exposing the treated surface to moisture to release chlorine dioxide from the composite into the atmosphere surrounding the material. The composites which are described in the '826 patent comprise a hydrophilic material containing chlorite anions and a hydrophobic material containing an acid releasing agent.

U.S. published application 2000/0021819 A1 describes compositions and methods for disinfecting and deodorizing a treatment area with a chlorine dioxide producing composition which comprises a mixture of amorphous calcium silicate, a chlorite salt and an activator wherein the activator includes an acid. The chlorine dioxide producing compositions may be packaged as a tablet, permeable sachet, or a permeable patch attached to a plastic bag. The compositions generate chlorine dioxide when exposed to moisture.

SUMMARY OF THE EMBODIMENTS

In one embodiment, the present invention relates to an antimicrobial composite comprising:
  (A) a polymer mixture comprising a mixture of at least one styrene polymer and at least one urethane polymer, and
  (B) an antimicrobial composition which comprises at least one metal chlorite and at least one hydrophilic material capable of reacting with the metal chlorite when exposed to water.

In another embodiment, this invention relates to films prepared from the above composites. In yet another embodiment, the invention relates to an adhesive labelstock comprising:
  (A) a polymer film substrate comprising a mixture of at least one styrene polymer and at least one urethane polymer, said substrate having a first surface and a second surface, and
  (B) an adhesive layer underlying the second surface of the substrate, wherein the substrate, or the adhesive layer, or both the substrate and the adhesive layer contain an antimicrobial composition which comprises at least one metal chlorite and at least one hydrophilic material capable of reacting with the metal chlorite when exposed to water.

The composites, films, adhesive labelstocks and labels of the present invention are effective in generating desirable amounts of chlorine dioxide gas over a desirable period of time when exposed to water or water vapor. The composites, films and labels are useful in releasing chlorine dioxide gas to prevent or retard microbial growth within an atmosphere or within an enclosure for a sustained period of time, and, therefore, the composites, films and labels can be utilized to control microbial growth on fruits such as strawberries contained in a package. In one particular embodiment of the present invention, a film or adhesive label including the film is utilized to deliver an antimicrobial composition to a package container. In another embodiment, the composites, films, labelstocks and labels of the invention can be utilized to sterilize objects such as baby bottles, medical devices, etc.

DESCRIPTION OF THE INVENTION

The term "overlies" and cognate terms such as overlying and the like, when referring to the relationship of one or a first layer relative to another or a second layer, refers to the fact that the first layer partially or completely overlies the second layer. The first layer overlying the second layer may or may not be in contact with the second layer. For example, one or more additional layers may be positioned between the first and the second layer. The term "underlies" and cognate terms such as "underlying" and the like have similar meanings except that the first layer partially or completely lies under, rather than over the second layer.

The term "transparent" when referring to one or more layers of the label film means that any material beneath such layers can be seen through such layers. In reference to the use of "transparent" or "clear" labels applied to clear containers, such as beer bottles, the bottle and the beer within the bottle are visible through the label.

The term "clear" when referring to one or more layers of the label or to the label itself means the opacity of the layers or label is less than about 5%, and the layers or the label has a haze of less than about 10%. Opacity is measured in accordance with TAPPI Test T425 os, and haze is measured in accordance with ASTM Test Method D-1003.

In one embodiment, the invention is an antimicrobial composite which comprises:

(A) a polymer mixture comprising a mixture of at least one styrene polymer and at least one urethane polymer, and (B) an antimicrobial composition which comprises at least one metal chlorite and at least one hydrophilic material capable of reacting with the metal chlorite when exposed to water.

In one embodiment, the polymer mixtures which are useful in the antimicrobial composites of the present invention may comprise from about 10 to about 90% by weight of at least one styrene polymer and from about 90 to about 10% by weight of at least one urethane polymer. In another embodiment, the polymer mixture comprises from about 40% to about 60% by weight of at least one styrene polymer and from about 40% to about 60% by weight of at least one urethane polymer.

The styrene polymers which can be utilized in the composites of the present invention include homopolymers as well as copolymers of styrene and substituted styrene such as alpha-methyl styrene. An example of a useful styrene homopolymer is Styron 615 APR which is available from Dow Plastics. This polystyrene is characterized as having a specific gravity of about 1.040 (ASTM D792), and a melt flow rate (ASTM D1238) of 14.00 g/10 min. A variety of styrene copolymers and terpolymers also may be utilized in the present invention, and these include acrylonitrile-butene-styrene (ABS); styrene-acrylonitrile copolymers (SAN); styrene butadiene (SB); styrene-malaeic anhydride (SMA); styrene-isoprene styrene (SIS); styrene-methyl methacrylate (SMMA); etc. Useful styrene terpolymers include a variety of SBS and SIS terpolymers available from Kraton Polymers under the general trade designation KRATON Polymers. Specific examples of useful KRATON Polymers include Kraton D1101, an SBS linear terpolymer and Kraton D1107 P, a linear SIS terpolymer. Another useful styrene copolymer is KR-10 from Philipps Petroleum Company, and KR-10 is believed to be a copolymer of styrene with 1,3-butadiene.

The composites of the present invention also comprise at least one polyurethane, and the polyurethanes include aliphatic polyurethanes as well as aromatic polyurethanes. Polyurethanes are typically the reaction products of (A) a polyisocyanate having at least two isocyanate (—NCO) functionalities per molecule with (B) at least one isocyanate reactive group such as a polyol having at least two hydroxy groups or an amine. Suitable polyisocyanates include diisocyanate monomers and oligomers.

In one embodiment, useful polyurethanes include aromatic polyether polyurethanes, aliphatic polyether polyurethanes, aromatic polyester polyurethanes, aliphatic polyester polyurethanes, aromatic polycaprolactam polyurethanes, and aliphatic polycaprolactam polyurethanes. Particularly useful polyurethanes include aromatic polyether polyurethanes, aliphatic polyether polyurethanes, aromatic polyester polyurethanes, and aliphatic polyester polyurethanes. Examples of commercially available and useful polyurethanes include a variety of thermoplastic polyurethanes available from Noveon, Inc. under the general designation Estane. Particular examples include Estane 5701 F1 which is an aromatic polyester-based polyurethane polymer; Estane 5702 which is an aromatic polyester-based polyurethane polymer; Estane 5703 which is an aromatic polyester based polyurethane polymer; Estane 5707 F1 which is an aromatic polyester-based polyurethane polymer; Estane 5712 F30 which is an aromatic polyester-based polyurethane polymer; Estane 5713 F2 which is an aromatic polyester-based polyurethane; Estane 5714 F1 which is an aromatic polyether-based polyurethane polymer and Estane 58213 NAT which is a polyester based thermoplastic polyurethane.

Useful polyurethanes are also available from other commercial sources such as from Avecia under the trade designation NeoRez and from Noveon under the designation Sancure. Examples of other aliphatic polyether polyurethanes commercially available include Sancure 2710®, Sancure 878®, NeoRez R-600, NeoRez R-966 and NeoRez 967. Examples of commercially available polyester polyurethanes include Sancure 2060 (polyester polyurethane), Sancure 2255 (polyester polyurethane), Sancure 815 (polyester-polyurethane), Sancure 878 (polyether-polyurethane), and Sancure 861 (polyether-polyurethane), NeoRez R-974 (polyester polyurethane), NeoRez R-981 (polyester-polyurethane) and NeoRez R-970 (polyether-polyurethane).

The antimicrobial compositions which are useful in the composites, films, adhesive labelstocks and labels of the present invention comprise at least one metal chlorite and at least one hydrophilic material capable of reacting with the metal chlorite when exposed to water. In one embodiment, the antimicrobial composition is free of hydrophobic materials. A variety of metal chlorites may be utilized in preparing the antimicrobial compositions, including alkali metal chlorites, alkaline earth metal chlorites and transitional metal chlorites. In one embodiment, the metal chlorites are alkali metal chlorites such as sodium chlorite and potassium chlorite. In another embodiment, alkaline earth metal chlorites can be employed, and examples of such chlorites include barium chlorite, calcium chlorite and magnesium chlorite.

The metal chlorites are available from a variety of commercial sources. Technical grade flaked sodium chlorite (80%) is available from Acros, Aldrich Chemical Co., and Alfa Asser. Calcium chlorite and potassium chlorite are available from T.J. Baker Co. and Aldrich Chemical Co., respectively. Generally, these commercial chlorites are dried (e.g., at 300° C. for 3 hours) and cooled prior to use.

A variety of hydrophilic materials can be included in the antimicrobial compositions utilized in the present invention. In one embodiment, the hydrophilic material is a dry solid hydrophilic material, and in another embodiment, the hydrophilic material is a dry solid inorganic hydrophilic material. In yet another embodiment, the dry solid hydrophilic material utilized in the preparation of the antimicrobial compositions is an acidified inorganic hydrophilic material which produces a pH of no more than about 10.5 when the aqueous portion of a 30 weight percent mixture of that material in deionized water is measured. In other embodiments, the solid hydrophilic materials useful in the present invention may produce a pH of less than 9 or even less than 7. Examples of dry solid hydrophilic materials suitable for reacting with the metal chlorite include synthetic zeolites such as zeolite A, zeolite X zeolite Y and mordenite; natural zeolites such as chabazite and clinoptilolite; natural zeolites such as chabazite and clinoptilolite; hydrous clays, such as bentonite, kaolin, attapulgite and halloysite; calcined clays, such as metakaolin, spinel phase kaolin, calcined bentonite, calcined halloysite, and calcined attapulgite; acidified synthetic zeolites, such as zeolite A, zeolite B, zeolite C, and mordenite that have been contacted with one or more acidic solutions containing sulfuric acid, hydrochloric acid, nitric acid, or other acidic compound (e.g. calcium chloride) so that the pH of the resulting aqueous phase of the mixture is below 10.5; acidified natural zeolites such as chabazite and clinoptilolite; acidified calcined clays, such as bentonite, kaolin, attapulgite and halloysite that have been contacted with one or more acidic solutions containing sulfuric acid, hydrochloric acid, nitric acid, or other acidic compounds (e.g. lanthanum chloride) so that the pH of the resulting aqueous phase of the mixture is below 10.5; acidified calcined clays, such as metakaolin, spinel phase kaolin, calcined bentonite, calcined halloysite, and calcined attapulgite that have been contacted with one or more acidic solutions containing sulfuric acid, hydrochloric acid, nitric acid, or other acidic compounds (e.g. acetic acid) so that the pH of the resulting aqueous phase of the mixture is below 10.5; salts, such as aluminum sulfate, magnesium sulfate, calcium carbonate, and particularly deliquescent acidic salts, such as calcium chloride, magnesium chloride, lithium chloride, and magnesium nitrate; solid acids, such as boric acid, tartaric acid and citric acid; organic acid anhydrides such as phthalic anhydride, maleic anhydride, succinic anhydride and glutaric anhydride; and mixtures of two or more thereof.

In one embodiment, the hydrophilic material comprises metakaolin microspheres. As used herein the term "microspheres" refers to nominally spherical particles having an average particle size of from about 50 to 100 microns. Metakaolin microspheres are comprised substantially of metakaolin and may be prepared by the procedures described in U.S. Pat. No. 6,077,495 which is incorporated in its entirety herein.

Metakaolin powder has a low surface area, as measured by the BET method. Thus, there is minimal microporosity. When supplied in the form of spray dried microspheres, however, the surface area remains low but voids are created and the microspheres have an appreciable content of large pores (voids). Reference is made to U.S. Pat. No. 4,214,978, Kennedy et al. As disclosed in this and other patents, the surface area (BET, using nitrogen) is typically between 10 to 15 $m^2/g$ but total pore volume (reflecting voids) is in the range of 0.06 cc/g to 0.09 cc/g. The microspheres produce an acidic pH in the liquid portion of an aqueous slurry of microspheres.

Metakaolin microspheres can be prepared by spray drying an aqueous slurry of white hydrous Georgia kaolin clay having a solids content of about 28-44% and a particle size distribution of about 80% by weight finer than one micron, and dispersing up to 2% by weight of the dried clay in a 25% to 30% solution of sodium silicate having a molar ratio of $SiO_2:Na_2O$ of 2.0 to 3.3 using a wheel atomizing spray dryer to produce spherical kaolin agglomerates having an average particle size of about 70 microns. The agglomerates are calcined in a rotary calciner for a time and temperature sufficient to convert substantially all of the hydrous kaolin to metakaolin (e.g. one hour at 700° C.).

Microspheres of kaolin clay that are calcined through the characteristic kaolin exotherm can be produced in a similar fashion to the procedure for preparing metakaolin microspheres described above, except that the calcination temperature is higher (e.g. one hour at 1,000° C.). The hydrous kaolin clay undergoes the characteristic exothermic transformation to the well-known spinel phase of kaolin without the formation of a substantial quantity of mullite. The resulting material is called "spinel phase microsphere".

Acid treated metakaolin microspheres can be prepared by applying a mineral acid such as sulfuric acid by spraying or other means which do not significantly alter the physical form of the microspheres. This may be followed by drying at temperatures below which any generated aluminum salts would decompose. For example, acid treated metakaolin microspheres may be prepared by impregnating about 300 grams of metakaolin microspheres prepared as above with 280 grams of 2.16 N sulfuric acid solution, drying at 100° C., and calcining at 350° C. for 3 hours.

The amount of the metal chlorite and the hydrophilic material in the antimicrobial compositions will depend on several factors, including, but not limited to, the quantity of chlorine dioxide gas desired for a particular application, the basicity of the metal chlorite, and the acidity of the hydrophilic material. In general, sufficient metal chlorite should be included in the composite to provide the desired rate of release. In one embodiment, the weight ratio of metal chlorite to hydrophilic material is in the range of from about 0.001:1 to about 0.25:1 or from about 0.01:1 to about 0.2:1. An example of a composition for producing a slow release ratio of long duration is a mixture of about 5% by weight of a metal chlorite and about 95% by weight of the hydrophilic material. A composition of higher release rate for shorter duration is a mixture of about 5% by weight sodium chlorite, 10% by weight chlorinated calcium chlorite and 85% by weight of acid treated metakaolin microspheres.

The antimicrobial compositions used in the present invention may optionally contain other materials. In one embodiment, the compositions may contain at least one desiccant which absorbs water to minimize or eliminate an initial production of chlorine dioxide gas due to residual water vapor present in the atmosphere or in the solids when the composition is prepared. Suitable desiccants include activated calcium chloride, activated calcium sulfate, activated zeolite X, activated zeolite A, activated bentonite clay, activated silica gel, activated attapulgite and mixtures thereof. The term "activated" means that the particular material has been substantially dehydrated by heating at an elevated temperature. For example, an activated material may be prepared by heating at 300° C. for about one hour. The total amount of desiccant included in the antimicrobial compositions used in the present invention may vary depending upon several factors such as ambient humidity and the water permeability of the packaging material used to contain the antimicrobial composition. In one embodiment, the desiccant may be present in an amount of from about 0.1% to about 25% by weight based on the total weight of the mixture.

The antimicrobial composition comprising a metal chlorite and a hydrophilic material can be formulated in several ways. One method is to prepare, in a dry atmosphere, an intimate physical mixture of fine powders of both constituents having particle sizes preferably below about 200 μm. Larger particles may be used and may achieve a slower rate of chlorine dioxide gas release in certain instances.

The mixture also can be formed by combining one of the constituents in liquid form with the other constituent(s). For example, a slurry of a fine powder of calcined kaolin microspheres in a nonpolar liquid such as dodecane may be combined with the metal chlorite. The mixture is then dried to remove the nonpolar liquid. If water is used as the liquid, then the mixture should be quickly dried to a sufficient extent to prevent excessive release of chlorine dioxide gas.

As mentioned above, the antimicrobial compositions useful in one embodiment of the invention can be prepared by methods described in U.S. Pat. No. 6,077,495 which is incorporated by reference. Specific methods of preparing antimicrobial composition based on metakaolin microspheres are illustrated in Examples 1 and 7 of the '495 patent. Antimicrobial compositions comprising a metal chlorite and a hydrophilic material capable of reacting with the chlorite when exposed to water are available commercially from Engelhard Corporation under the designation Aseptrol. Specific examples include Aseptrol 7.05F wherein the hydrophilic material is believed to be metakaolin microspheres and Aseptrol 1.05.

The antimicrobial composites of the present invention may be obtained, in one embodiment, by preparing a solution of a styrene polymer and the urethane polymer in one or more volatile organic solvents, and thereafter adding the antimicrobial composition to the solution to form a homogenous mixture.

When the urethane polymer and the styrene polymer are not mutually soluble in an organic solvent, the urethane polymer is dissolved in an organic solvent such as tetrahydrofuran or cyclohexanone, and the styrene polymer is dissolved in a solvent such as toluene to form two solutions which are thereafter blended. The antimicrobial composition is then added (with mixing) to the combined solutions to form a uniform mixture. The solvent(s) can be subsequently removed. Alternatively, the composite can be prepared by dry blending the styrene polymer, the urethane polymer and the antimicrobial composition.

The following are examples of the preparation of antimicrobial composites of the present invention.

EXAMPLE A

A solution of 8.11 grams of Estane 5714 polyurethane in 48.63 grams of tetrahydrofuran solvent is prepared. A second solution is prepared by dissolving 8.11 grams of Styron 615 in 18.93 grams of toluene. The two dissolved solutions are combined, and 16.22 grams of Aseptrol 7.05F powder are added to the combined solutions. The total mixture is mixed for an additional 30 minutes to form a uniform mixture.

EXAMPLE B

A first solution of 75 grams of Estane 5714 dissolved in 449.5 grams of tetrahydrofuran solvent is prepared. A second solution is prepared by dissolving 75 grams of Styron 615 in 175 grams of toluene solvent. A third solution is prepared by mixing 174.83 grams of the first solution and 83.33 grams of the second solution, and to 60 grams of the third solution, there are added 17.43 grams of Aseptrol 7.05F powder with stirring until a homogenous mixture is obtained.

In one embodiment of the invention, the antimicrobial composites of the present invention may be formed into films having a thickness of from about 0.1 to about 20 mils, or from about 0.5 to about 10 mils. The films also may be characterized as having a coat weight of from about 25 to about 600 $g/m^2$ or from about 100 to about 500 $g/m^2$.

The films may be prepared, in one embodiment, by preparing a mixture of the antimicrobial compositions in a solution or solutions of the styrene polymer and urethane polymer as described above, and thereafter casting or coating the mixture onto a release liner where the coating is dried at an elevated temperature to remove the solvent(s). After drying, the film can be retained on the release liner, or the film can be removed from the release liner for use in the intended applications as described herein. Alternatively, the films can be prepared by melt extrusion of a dry blend of the styrene and urethane polymers, and the above described antimicrobial compositions. The films may be used as produced (i.e., unoriented) or the films may be monoaxially or biaxially oriented by stretching at an elevated temperature followed by annealing (heat setting) at a higher temperature. Such orientation procedures are known to those skilled in the art.

In one embodiment, there appears to be an advantage in preparing the antimicrobial films of the invention by solvent casting onto a release liner and drying the coating to form the film. Films prepared in this manner contain a significant amount of the particles of the antimicrobial composition at the surface of the film thus forming a roughened surface similar to sand paper. Improved release of chlorine dioxide is observed for such films when compared to similar films formed by extrusion.

Non limiting examples of coating techniques include slot die, air knife, brush, curtain, extrusion, blade, floating knife, gravure, kiss roll, knife-over blanket, knife-over roll, offset gravure, reverse roll, reverse smoothing roll, rod and squeeze roll coating. The antimicrobial composites of the present invention containing one or more solvents can be applied to the release liner at room temperature or at elevated temperatures, and the coatings may be subjected to higher temperatures to accelerate evaporation of the solvents. Temperatures as high as 150° C. have been found to be useful.

The films of the present invention have desirable moisture vapor transmission rates (MVTR) and porosities that allow moisture to penetrate into the polymer film to initiate chlorine dioxide production and emission into the surrounding area.

In one embodiment, the styrene and urethane polymers used in the present invention provide films, adhesive labelstocks and labels that have a moisture vapor transmission rate (MVTR) that permits sufficient moisture to enter the films, labelstocks and labels to generate acceptable levels of chlorine dioxide, and allows the chlorine dioxide to enter the atmosphere. Thus, in one embodiment, the individual styrene polymers and urethane polymers used in the invention are those that are capable of forming films having an MVTR in the range of from about 200 to about 3000 g/m²-day@37.8 C, 100% RH. In another embodiment, the mixture of styrene and urethane polymers used in the invention provide films having an MVTR in the range of 200 to about 2500 g/m².

Although the films of the invention can be prepared by extrusion of the composites or by casting a mixture of the composite in a solvent for the styrene and urethane polymers, followed by drying, it has been discovered that the casting method provides films having higher porosity. Moreover, with regard to the casting procedure, it has been discovered that the porosity of the films thus obtained may be modified as desired by varying the drying conditions and/or the concentration of the antimicrobial composition in the mixture being cast. In general, lower porosity films can be obtained utilizing lower temperatures and longer drying times, and higher porosity films can be obtained utilizing higher temperatures and shorter drying times. For example, a low porosity film can be obtained by drying the coating comprising the antimicrobial composites and one or more solvents at room temperature for about 40 minutes; at about 70° C. for about 15 minutes; and finally at 130° for 15 minutes. Medium porosity films can be obtained by drying the coatings at 50° C. for 15 minutes; 70° C. for 15 minutes; and finally at 130° C. for 15 minutes. High porosity films can be obtained by drying the coatings at 90° C. for 15 minutes, and finally at 130° C. for 15 minutes.

The porosity of the films of the invention may be determined by measuring the air porosity as described in ASTM Test D726. This test measures the length of time required for a given quantity of air to pass through the film sample. Thus, a lower number indicates a highly porous material whereas a higher number indicates a low porosity material. In one embodiment the Gurley porosity of the films may range from about 0.5 to about 20 or 25 seconds. In one embodiment, a highly porous film of the invention may have a Gurley porosity of from about 0.5 to about 8 seconds, and a low porosity film may have a Gurley porosity of from about 10 to about 20 seconds.

The following examples illustrate the preparation of films of the invention.

EXAMPLE 1

A film is prepared from the antimicrobial composite of Example A above by coating the mixture at a gap of 50 mils onto a 1.5 mil thick silicone release coated PET film. The film is dried for 20 minutes at 70° C. and for 10 minutes at 130° C. The coating weight of the film thus obtained is about 300 grams/m².

EXAMPLE 2

A film is prepared from the antimicrobial composite of Example B above by coating the mixture at a gap of 41.5 mils onto a 1.5 mil thick silicone release coated PET film. The film is dried at 70° C. for 20 minutes and at 130° C. for 10 minutes. The coating weight of the film thus obtained is about 300 g/m².

The antimicrobial composites and the films prepared from the antimicrobial composites are effective in providing controlled release of chlorine dioxide gas over an extended period of time. In one embodiment, it is desirable that the composites and films provide a quick and high level of chlorine dioxide when the composites and films initially are contacted with water. In one embodiment, it is desired that the antimicrobial composites and films of the present invention provide for a quick release of chlorine dioxide at levels of from about 5 to about 7 or 8 ppm followed by reduced levels over an extended period of time. For example, it is desirable in one embodiment that the level of chlorine dioxide in the atmosphere surrounding the composite or film be at least about 1 ppm for a period of up to about 180 hours or even 200 hours or more.

The following test procedure is used to evaluate the samples of the composites and films of the present invention. A sample (about 2 grams) of the specified material is placed in a 16 ounce glass jar with a ventilated plastic rubber sealing lid having 2 holes each having diameter of about 1 cm. The samples are maintained in a room with controlled humidity and temperature (about 40% relative humidity and 23° C.). The chlorine dioxide gas concentration in the jar is determined and recorded over a period of time using a Freedom 5000 Universal Analog Toxic Gas Transmitter from Scott/Bacharach Instruments containing a 0-10 ppm range chlorine dioxide sensor.

The above chlorine dioxide test is carried out on the film of Example 2 and the results are summarized in the following table. The film sample placed in the test jar weights 1.67 g.

TABLE

| Test Conditions | | | $ClO_2$ Concentration (ppm) |
|---|---|---|---|
| Elapsed Time (hrs) | % RH | Temp (° C.) | Film of Example 2 |
| 0.00 | 41.0 | 23.1 | 0.00 |
| 15.48 | 41.0 | 23.1 | 9.261 |
| 20.64 | 38.5 | 24.1 | 8.845 |
| 39.12 | 40.5 | 23.2 | 6.692 |
| 43.14 | 40.0 | 23.3 | 5.205 |
| 62.47 | 40.0 | 23.1 | 3.654 |
| 67.75 | 78.5 | 23.9 | 2.533 |
| 87.03 | 41.0 | 23.2 | 1.775 |
| 91.35 | 39.0 | 24.1 | 2.060 |
| 158.73 | 41.0 | 23.2 | 3.855 |
| 165.03 | 40.0 | 23.3 | 1.290 |
| 187.56 | 41.0 | 23.3 | 1.072 |
| 207.33 | 39.0 | 24.0 | 0.761 |
| 211.43 | 39.0 | 24.1 | 0.856 |
| 235.19 | 41.0 | 23.3 | 0.907 |
| 254.74 | 41.0 | 23.2 | 0.761 |
| 327.48 | 41.0 | 23.1 | 0.361 |
| 357.24 | 40.5 | 23.1 | 0.366 |

In another embodiment, the present invention relates to an adhesive labelstock having antimicrobial properties, said labelstock comprising:

(A) a polymer film substrate comprising a mixture of at least one styrene polymer and at least one urethane polymer, said substrate having a first surface and a second surface, and (B) an adhesive layer underlying the second surface of the substrate wherein the substrate, or the adhesive layer, or both the substrate and the adhesive layer contain an antimicrobial composition which comprises at least one metal chlorite and at least one hydrophilic material capable of reacting with the metal chlorite when exposed to water.

In one embodiment, the antimicrobial composition is present in the polymer film substrate, and such polymer film substrates as described above can be utilized in preparing the adhesive labelstocks. Alternatively, the antimicrobial compositions can be included in the adhesive layer to provide the desired levels of released chlorine dioxide. Generally, however, the adhesive-containing labels of the present invention comprise a polymer film substrate containing an effective amount of the antimicrobial compositions described herein, and an adhesive layer underlying the substrate. The polymer film substrate of the adhesive labelstocks of the invention has a moisture vapor transmission rate and a porosity that are sufficient (a) to allow moisture to penetrate into the polymer substrate film which initiates the generation of chlorine dioxide and (b) to enable the thus formed chlorine dioxide to enter the atmosphere around the label.

The adhesive layer may be directly coated on the second surface of the substrate, or the adhesive layer may be transferred from a release liner with which the film substrate is combined. Alternatively, a composite of the polymer film substrate and the adhesive layer can be formed by coextrusion of the film substrate and the adhesive.

In one embodiment, the adhesive layer has a thickness in the range of from about 0.1 to about 2 mils (2.5 to 50 microns). Adhesives suitable for use in the adhesive labelstocks and labels of the present invention are commonly available in the art. Generally, these adhesives include pressure-sensitive adhesives, heat-activated adhesives, hot melt adhesives, and the like. Pressure-sensitive adhesives are particularly useful. These include acrylic based adhesives as well as other elastomers such as natural rubber or synthetic rubbers containing polymers or copolymers of styrene, butadiene, acrylonitrile, isoprene and isobutylene. Pressure-sensitive adhesives are well known in the art and any of the known adhesives can be used with the film substrates of the present invention. In one embodiment, the pressure-sensitive adhesives are based on copolymers of acrylic acid esters, such as, for example, 2-ethyl hexyl acrylate, with polar comonomers such as acrylic acid.

Heat activated adhesives become tacky when heated which allows the label to bond to a substrate. Materials useful for this purpose include but are not limited to the following film forming materials used alone or in combination: polyethylene, metallocene catalyzed polyolefins, syndiotactic polystyrene, syndiotactic polypropylene, cyclic polyolefins, polyethylene ethyl acrylate, polyethylene methyl acrylate, ABS polymers, polyethylene vinyl alcohol, polybutylene, polystyrene, polyurethane, polycarbonates, styrene acrylonitrile polymers, ionomers based on zinc or sodium salts of ethylene/methacrylic acid, fluoroplastics, etc.

In the manufacture of adhesive labelstocks and labels from the above-described film substrates in accordance with the invention, liner or carrier stock may be provided. The liner or carrier stock may comprise a multilayer liner made for example as disclosed in U.S. Pat. No. 4,713,273, the disclosure which is incorporated herein by reference, or may be a conventional liner or carrier consisting of a single paper of film layer which may be supplied in roll form. If it has not been previously provided with a release coating and does not itself include components to inherently generate a release surface at its adhesive-contacting face, the liner or carrier may be coated with a release coating (e.g., a silicone). If a release coating is applied, it is dried or cured following application by any suitable means.

The release face of the release liner or carrier may be coated with a layer of pressure-sensitive adhesive for subsequent transfer of the adhesive to the film substrate with which the liner or carrier is employed. When the film substrate is combined with the liner or carrier, the adhesive is joined to the film substrate. Later, the liner or carrier is removed to expose the adhesive, and the adhesive remains permanently joined to the film substrate.

In some applications, the adhesive layer may be a heat-activated adhesive or a hot-melt adhesive such as used in in-mold label applications, as distinguished from a pressure-sensitive adhesive. If the adhesive is a heat-activated adhesive or a hot-melt adhesive, there may be no need for a release liner for inherent releasability such as is required when using a pressure-sensitive adhesive.

The present invention also relates to printed films and printed adhesive labelstocks, both of which contain a print image on the first surface of the polymer substrates described above. Examples of print images include data or pictorial designs such as variable imprinted data such as serial numbers, bar codes, trademarks, etc. High quality printed constructions are prepared by running the films and labelstocks through a printer and printing an image on the first surface of the film or polymer substrate. A variety of printer technologies can be utilized including, without limitation, flexo/water based inks, UV letter press, UV flexo, UV silk screen, piezoelectric printer heads, thermal ink transfer, laser, etc. The labelstocks of the present invention may be printed at a printing station prior to being die-cut into individual labels. The printing step may occur before or after combining the liner and film substrate, but the printing generally will precede the die-cutting of the film substrate into individual labels. The film substrate must remain in accurate register between the printing steps (for example, between the successive impressions of different colors) in order that the image or text can be of high quality, and between printing and subsequent die-cutting in order that the image or text be properly located on the labels.

In some embodiments, the adhesive labelstocks of the present invention may be die-cut into labels, and in some embodiments, the labelstocks of the present invention are die-cuttable into a series of spaced adhesive labels carried by the release liner. The die-cutting step may be performed by rotary cutting dies in the well known manner and involves the subsequent stripping of the ladder-shaped matrix ("matrix stripping") of waste or trim surrounding the formed labels when they are die-cut (the "rungs" of the ladder representing the spacing between successive labels). The labels then remain on the liner in spaced relation with each other. The adhesive labels may be removed subsequently from the liner and applied either manually or mechanically to a substrate or article as desired. The labels may be of any desirable size and shape.

Although not necessary, in some applications it may be desirable to apply a transparent protective topcoat or overcoat on at least one surface of the films of the present invention or on the first surface of the polymer film substrate of the labelstocks and labels of the present invention. The topcoat provides an optional additional method for controlling the moisture penetration into the film or the polymer film substrate of the labelstocks and labels, and also provides a mechanism for controlling the release rate of the chlorine dioxide. The topcoat also provides a method for preventing or reducing premature exposure to moisture for a shelf stable product. The presence of a transparent topcoat layer may also provide additional protection for any print image which may be present on the surface of the film or on the first surface of the polymer film substrate of the labelstocks and labels of the invention.

The topcoat layer may be applied to the surface of the film or the first surface of the polymer film substrate of the labelstocks and labels of the invention by techniques known to those skilled in the art. The topcoat polymer film may be deposited from a solution, applied as a preformed film, etc. When a transparent topcoat or overcoat layer is present, it may comprise a single layer or a multilayer structure. The thickness of the topcoat layer may be in the range of from about 0.5 to about 5 mils, and in one embodiment, from about 1 to about 3 mils.

The topcoat layer may comprise any film-forming monomer, oligomer, or polymer or combinations thereof. These materials may be water soluble, organic solvent soluble, or insoluble in water and organic solvents since the coating compositions may be applied as solutions, dispersions or emulsions. Non limiting examples of useful topcoat materials include polyurethanes, polyolefins, polyacryls, polymethacryls, polyamides, polyvinyl acetates, polyvinyl alcohols, polyvinyl ethers, polyacrylonitriles, polystyrenes, polyvinyl pyrollidones, polyvinyl chlorides, poly(alkylene oxides), proteins, cellulosic polymers, gelatin, and copolymers of one or more monomers including olefins, (meth)acrylates, vinyl acetates, allyl acetates, vinyl chlorides, acrylonitriles, N-vinyl pyrollidones, vinyl ethers, and other allylic and vinylic monomers. Examples of useful topcoat materials also are described in U.S. Pat. No. 6,106,982 which is incorporated herein by reference.

The composites, films, labelstocks and labels of the invention which have been described herein can be used for the treatment of odors and microbes in a number of applications, particularly in the vicinity of food products (for example fruits), medical devices, etc. The invention provides a variety of forms (i.e., composites, films and labels) through which the inventive antimicrobial materials can be applied directly to a treatment area. The composites which can be prepared, for example, by dry blending the components (i.e, the terpolymer and the antimicrobial composition) can be used as a powder or as a formed product such as a pallet or tablet film, or adhesive label. For example, a film or adhesive label of the present invention can be utilized to control microbial growth by placing a film or adhesive label in the area to be protected. In particular, films of the present invention can be utilized to control microbial growth within packages containing food products. For example, fresh produce such as strawberries has a short shelf life due to the growth of gray mold (botrytis cinerea) which is the principal cause of decay of the strawberries. In accordance with the present invention, the shelf life of strawberries contained in various containers such as a clam shell container is increased by introducing a piece of the film of the present invention or an adhesive label of the present invention into the package. The films, labelstocks and/or labels of the present invention also can be utilized to sterilize objects placed into a closed container. For example, objects to be sterilized can be placed into a container which also contains a sufficient amount of the composite of the invention to provide the required amount of chlorine dioxide when the composite is exposed to moisture within the closed container. Objects which can be sterilized in this manner include baby bottles, feeding spoons, and various medical devices.

While the invention has been explained in relation to its various embodiments, it is to be understood that other modifications thereof will become apparent to those skilled in the art upon reading the specification. Therefore, it is to be understood that the invention disclosed herein is intended to cover such modifications as fall within the scope of the appended claims.

The invention claimed is:

1. An adhesive labelstock comprising:
   (A) a polymer film substrate comprising a mixture of at least one styrene polymer and at least one urethane polymer wherein the polymer film substrate has a moisture vapor transmission rate that permits sufficient moisture to enter the film or labelstock to generate acceptable levels of chlorine dioxide, and said substrate has a first surface and a second surface, and
   (B) an adhesive layer underlying the second surface of the substrate, wherein the substrate contains an antimicrobial composition which comprises at least one metal chlorite and at least one hydrophilic material capable of reacting with the metal chlorite when exposed to water.

2. The labelstock of claim 1 wherein the hydrophilic material is an inorganic hydrophilic material.

3. The labelstock of claim 1 wherein the hydrophilic material comprises hydrous clays, calcined clays, acidified clays, acidified calcined clays, and mixtures of two or more thereof.

4. The labelstock of claim 1 wherein the hydrophilic material is an inorganic material comprising natural zeolites, synthetic zeolites, acidified synthetic zeolites, acidified natural zeolites and mixtures of two or more thereof.

5. The labelstock of claim 1 wherein the antimicrobial composition comprises at least about 5% by weight of the metal chlorite, based upon the total weight of the composition.

6. The labelstock of claim 1 wherein the metal chlorite is selected from alkali metal chlorites, alkaline earth metal chlorites and mixtures thereof.

7. The labelstock of claim 1 wherein the metal chlorite is sodium chlorite or potassium chlorite.

8. The labelstock of claim 1 wherein the hydrophilic material is an acidified clay comprising at least one bentonite, kaolin, attapulgite and halloysite that has been contacted with one or more acidic solutions.

9. The labelstock of claim 1 wherein the hydrophilic material is an acidified calcined clay comprising metakaolin, spinel phase kaolin, calcined bentonite, calcined halloysite, calcined attapulgite and a mixture of two or more thereof that has been contacted with one or more acid solutions.

10. The labelstock of claim 1 wherein the hydrophilic material comprises metakaolin microspheres.

11. The labelstock of claim 1 wherein the antimicrobial composition also contains a desiccant.

12. The labelstock of claim 1 wherein the antimicrobial composition is in the substrate.

13. The labelstock of claim 1 wherein the antimicrobial composition is present in the polymer substrate at a concentration of from about 10 to about 75% by weight based on the total weight of the antimicrobial composition and the polymer substrate or adhesive layer containing the antimicrobial composition.

14. The labelstock of claim 1 wherein the antimicrobial composition is free of hydrophobic materials.

15. The labelstock of claim 1 wherein the adhesive layer comprises a heat activated adhesive or a pressure sensitive adhesive.

16. An adhesive-containing labelstock comprising:
   (A) a polymer film substrate comprising a mixture of at least one styrene polymer and at least one urethane polymer, and an effective amount of a antimicrobial composition which comprises at least one metal chlorite and at least one solid inorganic hydrophilic material capable of reacting with the metal chlorite when exposed to water, said substrate having a moisture vapor transmission rate that permits sufficient moisture to enter the film or labelstock to generate acceptable levels of chlorine dioxide, and said substrate has a first surface and a second surface, and
   (B) an adhesive layer underlying the second surface of the substrate.

17. The labelstock of claim 16 wherein the antimicrobial composition is free of hydrophobic materials.

18. The labelstock of claim 16 wherein the hydrophilic material comprises from hydrous clays, calcined clays, acidified clays, acidified calcined clays, and mixtures of two or more thereof.

19. The labelstock of claim 16 wherein the hydrophilic material is an inorganic material comprising natural zeolites, synthetic zeolites, acidified synthetic zeolites, acidified natural zeolites and mixtures of two or more thereof.

20. The labelstock of claim 16 wherein the antimicrobial composition comprises at least about 5% by weight of the metal chlorite, based upon the total weight of the composition.

21. The labelstock of claim 16 wherein the metal chlorite comprises alkali metal chlorites, alkaline earth metal chlorites and mixtures of two or more thereof.

22. The labelstock of claim 16 wherein the metal chlorite is sodium chlorite or potassium chlorite.

23. The labelstock of claim 16 wherein the hydrophilic material is an acidified clay selected from bentonite, kaolin, attapulgite, halloysite or a mixture thereof that has been contacted with one or more acidic solutions whereby the acidified hydrophilic material produces a pH of no greater than 10.5 when the aqueous portion of a 30 weight percent mixture of the hydrophilic material in deionized water is measured.

24. The labelstock of claim 16 wherein the hydrophilic material is an acidified calcined clay comprising metakaolin, spinel phase kaolin, calcined bentonite, calcined halloysite, calcined attapulgite or a mixture of two or more thereof that has been contacted with one or more acid solutions whereby the acidified hydrophilic material produces a pH of no greater than 10.5 when the aqueous portion of a 30 weight percent mixture of the hydrophilic material in deionized water is measured.

25. The labelstock of claim 16 wherein the hydrophilic material comprises metakaolin microspheres.

26. The labelstock of claim 16 wherein the polymer substrate comprises from about 25 to about 75% by weight of the antimicrobial composition based on the total weight of the polymer substrate.

27. The labelstock of claim 16 wherein the adhesive layer comprises a heat activated adhesive or a pressure sensitive adhesive.

28. The labelstock of claim 16 wherein the adhesive layer comprises a pressure sensitive adhesive.

29. The labelstock of claim 16 further comprising
(C) a protective polymeric topcoat layer having a first surface and a second surface wherein the second surface is in contact with the first surface of the polymer substrate.

30. The labelstock of claim 29 wherein the antimicrobial composition is free of hydrophobic materials.

31. The labelstock of claim 29 wherein the hydrophilic material comprises hydrous clays, calcined clays, acidified clays, acidified calcined clays, and mixtures of two or more thereof.

32. The labelstock of claim 29 wherein the antimicrobial composition comprises at least about 5% by weight of the metal chlorite, based upon the total weight of the composition.

33. The labelstock of claim 29 wherein the metal chlorite comprises alkali metal chlorites, alkaline earth metal chlorites and mixtures of two or more thereof.

34. The labelstock of claim 29 wherein the metal chlorite is sodium chlorite or potassium chlorite.

35. The labelstock of claim 29 wherein the hydrophilic material is an acidified clay comprising bentonite, kaolin, attapulgite, halloysite and mixtures of two or more thereof that have been contacted with one or more acidic solutions whereby the hydrophilic material produces a pH of no greater than 10.5 when the aqueous portion of a 30 weight percent mixture of the hydrophilic material in deionized water is measured.

36. The labelstock of claim 29 wherein the hydrophilic material is an acidified calcined clay comprising metakaolin, spinel phase kaolin, calcined bentonite, calcined halloysite, calcined attapulgite and mixtures of two or more thereof that have been contacted with one or more acid solutions whereby the hydrophilic material produces a pH of no greater than 10.5 when the aqueous portion of a 30 weight percent mixture of the hydrophilic material in deionized water is measured.

37. The labelstock of claim 29 wherein the hydrophilic material comprises metakaolin microspheres.

38. The labelstock of claim 29 wherein the antimicrobial composition is present in the polymer substrate at a concentration of from about 10 to about 75% by weight based on the total weight of the polymer substrate.

39. The labelstock of claim 29 wherein the adhesive layer comprises a heat activated adhesive or a pressure sensitive adhesive.

40. The labelstock of claim 29 wherein the upper surface of the topcoat layer is ink printable.

41. An adhesive label obtained by die-cutting the adhesive labelstock of claim 1.

42. An adhesive label obtained by die-cutting the adhesive labelstock of claim 16.

43. The adhesive labelstock of claim 1 wherein the polymer film substrate has a moisture vapor transmission rate of from about 200 to about 3000 g/m$^3$/day at 37.8° C., 100 RH.

44. The adhesive-containing labelstock of claim 16 wherein the polymer film substrate has a moisture vapor transmission rate of from about 200 to about 3000 g/m$^3$/day at 37.8° C., 100 RH.

45. The adhesive labelstock of claim 1 wherein the adhesive layer is in contact with the second surface of the substrate.

46. The adhesive containing labelstock of claim 16 wherein the adhesive layer is in contact with the second surface of the substrate.

* * * * *